United States Patent [19]

Mirviss

[11] Patent Number: 4,766,250
[45] Date of Patent: Aug. 23, 1988

[54] RACEMIZATION CATALYST FOR AMINO ACIDS

[75] Inventor: Stanley B. Mirviss, Stamford, Conn.

[73] Assignee: Stauffer Chemical Co., Westport, Conn.

[21] Appl. No.: 53,906

[22] Filed: Jul. 10, 1987

Related U.S. Application Data

[62] Division of Ser. No. 736,724, May 22, 1985, Pat. No. 4,713,470.

[51] Int. Cl.$^4$ .................... C07C 45/64; C07C 47/575; C08L 27/00

[52] U.S. Cl. ........................................ 568/433; 525/76; 525/151; 525/154; 526/208; 562/401; 568/442

[58] Field of Search ................... 568/433, 442; 525/76, 525/151, 154; 526/208; 562/401

[56] References Cited

U.S. PATENT DOCUMENTS

| | | | |
|---|---|---|---|
| 3,813,317 | 5/1974 | Benolton et al. | 562/401 X |
| 4,206,139 | 6/1980 | Idelson et al. | 568/442 X |
| 4,401,820 | 8/1983 | Chibata et al. | 562/401 X |

FOREIGN PATENT DOCUMENTS

| | | |
|---|---|---|
| 0089886 | 9/1983 | European Pat. Off. |
| 42-13445 | 7/1967 | Japan . |
| 657841 | 4/1979 | U.S.S.R. |
| 686754 | 9/1979 | U.S.S.R. |
| 929629 | 5/1982 | U.S.S.R. |

OTHER PUBLICATIONS

Toi et al., Bull. Chem. Soc. Jpn, 35, pp. 1422–1423, (Aug. 1962).
Toi et al., Bull Chem. Soc. Jpn, 36, pp. 734–737, 739–743, (Jun. 1963).
Yamashov et al., Polymer Sci. USSR, 21, 2031–2037, (Dec. 1980).
Biotechnology Letters, 7, 31–36, (Jan. 1985).

*Primary Examiner*—Werren B. Lone
*Assistant Examiner*—Vera C. Clarke
*Attorney, Agent, or Firm*—Michael J. Bradley; Paul R. Martin; Paul J. Juettner

[57] ABSTRACT

There is disclosed a process for the racemization of amino acids and derivatives thereof. The racemization process of the present invention uses an aromatic aldehyde-containing polymer made from the reaction of a hydroxyaromatic aldehyde with a chloromethylated vinylbenzene polymer under reaction conditions to form an aromatic aldehyde-containing polymer wherein the aldehydic moiety is linked to the polymer through an ether linkage. There is also disclosed a process for the production of the racemization catalyst. Another embodiment of the invention comprises a process for the promotion of the racemization reaction wherein a tertiary amine-containing resin is used as a promoting agent.

6 Claims, No Drawings

RACEMIZATION CATALYST FOR AMINO ACIDS

This is a division of application Ser. No. 736,724, filed May 22, 1985, now U.S. Pat. No. 4,713,470.

FIELD OF THE INVENTION

The present invention relates to improved processes for the racemization of amino acids and derivatives thereof.

BACKGROUND OF THE INVENTION

The use of alpha amino acids has recently undergone substantial development because of new uses uncovered in the areas of medicine and food. The preparation of L-alpha amino acids has become increasingly important particularly in view of the fact that the L-alpha amino acids have been shown in some instances to be more effective than the D-alpha amino acids. Further, with the development of the artificial sweetener aspartame, an increasing need has arisen for a precursor, L-phenylalanine.

Since racemates of D,L-alpha amino acids contain one-half of either isomer, resolution of the racemates into one isomer can have a theoretical yield of only 50 percent. The profitability of any resolution method is directly tied to methods for racemizing the residue left after resolution into a D,L-racemate for further resolution. Since resolution is generally the result of selectively changing a derivative of the desired isomer of the amino acid to the desired amino acid isomer, racemization of the remaining isomer derivative must be under conditions that allow formation of a racemate of the derivative for further resolution.

Many methods are known for racemization of free amino acids or their salts such as the aqueous system shown in U.S. Pat. No. 4,401,820. The patent teaches the use of an aldehyde and a glacial acetic acid-water mixture to effect racemization of amino acids. The patent does not provide direction for racemization of amino acids wherein the carbonyl group is substituted. The use of the aqueous media disclosed in this reference can also result in the hydrolysis of some amino acid derivatives, notably esters, resulting in the formation of an amino acid contaminated with aldehyde and acetic acid.

Very few methods are available for racemization of carbonyl-substituted amino acids which allow for the racemization without destruction of the carbonyl-substituent group. Of particular importance is European Patent Publication No. 0089,886 which teaches the use of an insolubilized pyridoxal-5-phosphate to racemize amino acid esters in aqueous media. The essential teaching of the reference is the ability to carry out the chemical catalytic racemization under the same reaction conditions of solvent, pH and temperature as that used for the enzymatic hydrolysis resolution. This patent teaches that an immobilized pyridoxal-5-phosphate can be used to racemize D-phenylalanine ester to the corresponding D,L-racemate in an aqueous solution at pH 7 and a temperature of preferably 20° to 40° C. This is in line with the fact that pyridoxal-5-phosphate is a biological component whose reactions are normally conducted in aqueous medium.

It is known that racemates of D,L-alpha amino acid ester can be hydrolytically resolved into the L-amino acid by use of various esterase enzymes such as chymotrypsin. This enzyme specifically forms the basis of a process for the enzymatic resolution of racemic mixtures of phenylalanine (U.S. Pat. No. 3,813,317). In this patent, chymotrypsin is used to hydrolytically resolve an aqueous racemic mixture of ring-substituted phenylalanine esters. The reaction is carried out in an aqueous solution.

The combination of an aliphatic acid and an aldehyde or ketone as a racemizing agent for esters of amino acids is disclosed in co-pending U.S. patent application Ser. No. 642,212 filed Aug. 17, 1984, now abandoned.

In co-pending U.S. patent application Ser. No. 641,889 filed Aug. 17, 1984, now abandoned, there is disclosed a process for racemizing derivatives of amino acids by heating the amino acid derivatives with pyridoxal-5-phosphate in an organic solvent system.

The advantages of using an organic solvent system in combination with pyridoxal-5-phosphate are discussed in the article by Pugniere et al. appearing in Biotechnology Letters 7, 31–6 (1985).

While the use of pyridoxal-5-phosphate in an organic solvent system as a racemizing agent does possess a number of advantages, this method can be expensive due to the cost of the pyridoxal-5-phosphate as well as the fact that upon prolonged storage, the pyridoxal-5-phosphate can exhibit a serious loss of racemizing activity.

Similarly, the racemization of amino acids or derivatives of amino acids in the presence of aliphatic or mineral acids may also present problems. The presence of the mineral acid can lead to the formation of the acid salt of the amino acid which must be first neutralized to destroy all acidity. This adds an extra reaction step and can result in some loss of amino acid. In the presence of aliphatic acids, amino acid esters tend to undergo peptidization unless they are present as the mineral acid salt. When either mineral and/or aliphatic acids are present, an extra neutralization step will be required and waste disposal of the salt formed in neutralization will also be required before any resolution process can be carried out.

Another method for the racemization of amino acids or amino acid derivatives involves the use of aromatic aldehydes combined with polymeric resins. A number of references disclose this method.

Russian Pat. No. 929,629 discloses the preparation of an aromatic aldehyde-containing polymeric resin wherein the aromatic aldehyde-containing polymeric resin is prepared by reacting a chloromethylated styrene-divinylbenzene copolymer with nitrobenzene solvent, salicylaldehyde and zinc chloride.

Previously discussed EPO patent application No. 0089886 discloses the use of pyridoxal-5-phosphate supported on diethylaminoethyl cellulose for the racemization of L-tyrosine methyl ester at pH 7.

In two Russian patents (USSR No. 593,733 and USSR No. 686,754), there is disclosed a racemization process for amino acids which uses an aromatic resin with hydroxy and aldehyde groups. The racemization is done in the presence of cupric ion. Similar to the above procedure are the methods reported in CA 92, 181930w [corresponding to the article appearing in Vysokomol. Sozed. A22(1), 71–6 (1980)], in Bull. Chem. Soc. Jpn. 35, 1422 (1962), in Bull. Chem. Soc. Jpn. 36, 734 (1963), and in Bull. Chem. Soc. Jpn. 36, 739 (1963).

The above methods suffer from the disadvantage of requiring the presence of a metallic ion. Thus, a second step is needed to remove the metallic ion, complete removal of which is not often possible.

Thus, there is a need for a racemization process which can effectively racemize amino acids or amino acid derivatives without the presence of aliphatic acids, mineral acids or metallic ions. Such a process would eliminate extra neutralization steps, negate the possibility of unwanted peptidization reactions and also eliminate the extra step of removal of metallic ions. There is also a need for the promotion of the racemization process so that complete racemization can be carried out in shorter periods of time using recoverable racemization agents which are storage stable with little to no loss in activity for recyclic use.

SUMMARY OF THE INVENTION

In accordance with the present invention, there is disclosed a process for the racemization of amino acids and derivatives thereof. The racemization process of the present invention uses an aromatic aldehyde-containing polymer made from the reaction of an hydroxyaromatic aldehyde with a chloroalkylated chloromethylated substituted e.g., vinylbenzene polymer under reaction conditions to form an aromatic aldehyde-containing polymer wherein the aldehyde moiety is linked to the polymer through an ether linkage. There is also disclosed a process for the production of the racemization catalyst. Another embodiment of the invention comprises a process for the promotion of the racemization reaction wherein a tertiary amine-containing resin is used as a promoting agent.

DETAILED DESCRIPTION OF THE INVENTION

The optical isomer of the alpha amino acid or derivatives thereof that is racemized in accordance with the present invention can be either the L-form, the D-form or mixtures thereof. As the theoretical ratio of the two isomers is 50:50, any mixture different than that ratio can be racemized. Any degree of racemization can be obtained in accordance with the present invention and thus it is considered that partial racemizations are included within the scope thereof. By partial racemization is meant that at least 10 percent of the largest quantity of optical isomer has been racemized. Preferably, at least 50 percent of the largest amount of optical isomer is racemized. By racemized is meant the conversion of the optically active form to an optically inactive form, consisting of an equal mixture of D and L-forms.

The present invention is directed to racemizing optically active isomers of amino acids or derivatives thereof. The carbonyl group or amino group of these acids can be substituted by any number of substituents.

These amino acids or substituted amino acids can be represented by the formula:

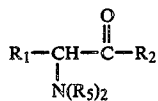

wherein $R_1$ can be straight or branched chain alkyl, mercaptoalkyl, carboxyalkyl, hydroxyalkyl, alkylthio, aminoalkyl, alkoxy, benzyl, aryl and indolylalkyl and the hydroxy, alkoxy, alkyl, halo and nitro substituted derivatives thereof; $R_2$ is selected from the group consisting of $YR_3$, wherein Y is oxygen or sulfur, or $NHR_4$; $R_3$ can be hydrogen or straight or branched chain aliphatic radicals having from 1 to about 8 carbon atoms, aryl of up to three fused rings and the hydroxy, halo, alkyl, alkoxy and nitro substituted derivatives thereof and $R_4$ and $R_5$ can be the same as defined in $R_3$ and hydrogen. As used herein the term "alkyl" used alone or in derivative form such as alkoxy, alkylthio, indolylalkyl and the like is intended to include groups having from 1 to about 8 carbon atoms. As used herein, the term "amino acid derivative" is intended to mean that the carbonyl group or amino group attached to the alpha carbon atom of the amino acid is substituted as is shown in the formula in this paragraph.

Examples of the represented parent amino acids, i.e. where $R_2$ is hydroxyl and $R_5$ is hydrogen, include valine, leucine, isoleucine, serine, threonine, methionine, phenylalanine, tyrosine, tryptophan, arginine, glutamic acid, lysine, 3,4-dihydroxyphenylalanine, 2,4-dihydroxyphenylalanine, 3,4-methylenedioxyphenylalanine; 3,4-dimethoxyphenylalanine; 3,4-isopropylidenedioxyphenylalanine; 3,4-cyclohexylidenedioxyphenylalanine, 5-hydroxytryptophan; 5-methyltryptophan and 3,4,5-trihydroxyphenylalanine.

The amino acids used in the invention are racemizable and can be in the form of substituted derivatives. The substituent group must not be of sufficient molecular weight or structure to interfere with the racemization process. Examples of the substituents groups include the preferred ester, as well as primary and secondary amides (wherein $R_2$ can be $-NH_2$, or $-NHR$), and thioesters (Y=S). The ester groups can be straight or branched chain aliphatic of from 1 to about 8 carbon atoms, aromatic up to three fused rings and substituted derivatives thereof such as halo, hydroxy, alkyl, alkoxy, nitro and the like. The amides are preferably straight or branched chain aliphatic amides of from 1 to about 8 carbon atoms. Preferably, the substituent group is the ester and preferably the ester is methyl or ethyl.

Preferably the amino acid is phenylalanine or ring-substituted derivatives thereof. The ring substituents can include hydroxy, alkoxy, halo, alkyl and nitro groups. The preferred substituent group is the ester. Preferably the ester is the methyl or ethyl ester.

The racemization reaction may be conducted in a suitable solvent. For instance, organic solvents such as toluene, methylene chloride, cyclohexanone, ethyl acetate, butyl acetate, butanol and the like may be used. If the substituted amino acid is the amino acid ester, it is preferred that an organic solvent be used.

The solution to be racemized can be prepared separately or it can occur as the result of a resolution process. The solution to be racemized can also be the result of a resolution reaction utilizing an organic solvent phase containing unhydrolyzed isomer.

In a preferred embodiment of the present invention, the solution to be racemized is the result of an enzyme hydrolysis process for resolving amino acids as their esters, e.g. D,L-phenylalanine ester, by the use of an organic-aqueous solvent system wherein a majority of the carbonyl-substituted amino acid concentrates in the solvent phase while the hydrolysis occurs in the aqueous phase.

As the racemization reaction is more conducive at elevated temperatures, it is preferred that the apparatus be adapted to allow for sufficient heating of the organic solvent systems. The apparatus can also be adapted as a means of increasing the temperature of reaction above that of reflux.

To effect racemization of the optical isomer, the present invention uses a novel racemization catalyst. The racemization catalyst of the present invention is prepared by reacting a hydroxyaromatic aldehyde with a chloromethylated vinylbenzene polymer or copolymer under reaction conditions such that the aromatic aldehyde becomes linked to the polymer through an ether linkage.

Examples of hydroxyaromatic aldehydes which can be used in the present invention include those corresponding to the formula

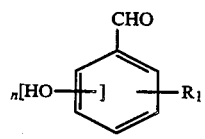

wherein $R_1$ can be a substituent group which is non-reactive under the conditions of the present reaction and n is an integer from 1 to 3. Examples of substituent groups which are non-reactive include alkyl groups of from 1 to about 5 carbon atoms, nitro, alkoxy and halo. The preferred hydroxyaromatic aldehyde is salicylaldehyde although other aromatic aldehydes containing free hydroxyl groups such as 3,4-dihydroxybenzaldehyde can also be used in the process of the present invention.

The chloromethylated vinylbenzene polymer has the general structure

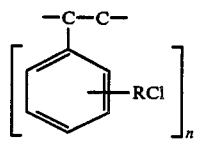

wherein R is an alkyl group, preferably methyl, and n is a number from 100 to about 1,000,000. Particularly suited for the process of the current invention are those polymers manufactured by Bio-Rad Laboratories and sold under the trade name BIOBEADS®, such as BIOBEADS® S-X1, chloromethyl. The BIOBEADS® S-X1, chloromethyl is a chloromethylated polystyrene resin which contains 1 percent divinylbenzene crosslinking and 4.25 meq of chloromethyl groups per gram of resin. Other suitable resins include those made by the polymerization of vinylbenzyl chloride such as the series 7055 resin manufactured by Polyscience, Inc.

Hereinafter, the term "chloromethylated vinylbenzene polymer" includes the above described resins as well as other resins containing divinylbenzene crosslinking and in addition, includes those vinylbenzene resins without divinylbenzene crosslinking.

It is particularly important that the aromatic aldehyde-containing polymer be formed under conditions which lead to the formation of an ether linkage between the aromatic aldehyde and the chloromethylated vinylbenzene polymer. In the present invention, it has been found that carrying out the condensation reaction in the presence of a base insures that the hydroxyaromatic aldehyde is conjugated to the vinylbenzene compound through an ether linkage. An exemplary reaction can be expressed as follows:

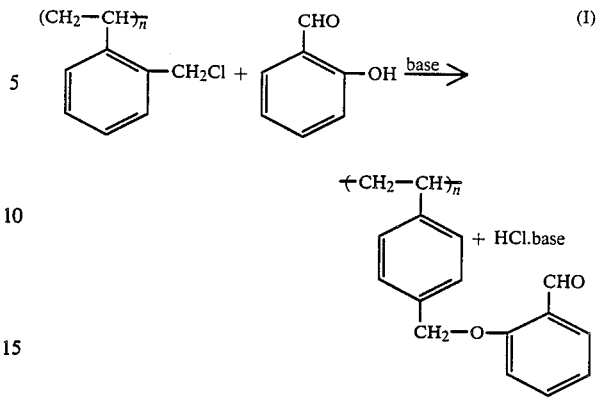

Polymer I, thus formed, exhibits surprising properties as a racemization catalyst. More specifically, polymer I is an aromatic aldehyde-containing vinylbenzene polymer which can act as a racemizing agent in aqueous or non-aqueous media without requiring the presence of a mineral acid, an aliphatic acid or metallic ions. Thus, usage of the unique racemization catalyst of the present invention eliminates a number of extra experimental steps. For instance, since a mineral acid is not required, no neutralization step is needed. Since the presence of an aliphatic acid is not required, there is eliminated the possibility of unwanted peptidization reactions and a neutralization step. Since the racemization catalyst of the present invention does not require the presence of metallic ions to effect racemization of the amino acids or derivatives thereof, the extra step of removal of the metallic ions is not required. Finally, the use of a resinous (polymeric) aldehyde prevents contamination of the racemate with aldehyde which may inhibit the enzyme used in the resolution process.

While forming no part of the present invention, it is theorized that the aromatic aldehyde-containing polymer linked to the polymeric compound through an ether linkage is a more effective racemization catalyst since it can more easily form a Schiff base, said reversible Schiff base formation being a necessary component of the racemizing process.

Examples of bases which can be used to form the present racemization catalyst include pyridine, potassium hydroxide, sodium hydroxide, lithium hydroxide, triethylamine, sodium methoxide and ammonia. The base is chosen based on the fact that it will remove the hydrogen chloride by-product formed when the chloromethylated polyvinylbenzene is reacted with the hydroxyaromatic aldehyde, thereby insuring the formation of the racemization catalyst having the desired ether linkage. The amounts of base used can range from about 100 mole % to about 300 mole % based on the amount of chloromethyl groups.

Usage of the racemization catalyst of the present invention enables the racemization of the amino acids or derivatives thereof to be effected in a shorter period of time than seen when using the racemization catalysts of the prior art.

The catalyst can be placed directly into the vessel containing the amino acid or derivative thereof to be racemized or the dissolved amino acid or derivative thereof can be pumped through a vessel containing the polymeric catalyst. As the racemization reaction is a high temperature reaction, it is preferred that the apparatus be adapted to allow heating at the same time that the catalyst is in contact with the amino acid or derivative thereof. Agitation may be required to allow even blending and uniform heat transfer.

The amount of the racemization catalyst can range from about 5 to about 100 wt. % based on the amount of amino acid or derivative thereof to be racemized. The concentration of the amino acid or derivative thereof in the solvent system can range from about 0.1 to about 60 wt. % with from about 0.5 to about 40 wt. % being preferred.

The temperature conditions within the system are such as to be conducive to the racemization reaction. The temperature of reaction can range from about 25° C. to about 135° C. and preferably from about 50° C. to about 125° C. and most preferably at the reflux temperature of the solvent. The reaction is preferably conducted at atmospheric pressure though pressures of up to 50 atmospheres may be used. The racemization reaction is conducted for a period of time sufficient to racemize at least 10 percent of the optical isomer of the larger quantity and preferably for a period of time sufficient to racemize at least 50 percent. The time for racemization generally ranges from about 1 to about 50 hours, though less or more time may be used.

The process of the invention can be operated as a batch process or as a continuous process, preferably in combination with an optical isomer resolution process. Portions of the organic phase can be withdrawn from the system either totally or in part depending on whether a batch process or a continuous process is being undertaken. It is not necessary that the racemization be undertaken on a pure optical isomer since blends of the D and L-isomers wherein one is substantially larger than the other can be racemized by the present invention to the limit of 50:50 D to L isomer.

If the amino acid derivative used is the carbonyl-substituted ester of the amino acid, it is desirable that the organic solvent, e.g. toluene, be essentially anhydrous to avoid hydrolyzing the carbonyl-substituted amino acid.

The racemate can be recovered in a form for further resolution. Also, the D,L-racemate can be directly recovered by conventional means such as distillation and crystallization.

In another embodiment of the present invention, it has been discovered that the racemization reaction can be effected in shorter time periods by using a promoting agent. Use of the promoting agent allows for a greater percentage of racemization in shorter periods of time, thus making the process more suitable for industrial use.

In previously discussed Russian Pat. No. 929,629, it is disclosed that the racemization rate can be increased by using tertiary amines as promoting agents. However, the tertiary amine will contaminate the carbonyl-substituted amino acid, thereby necessitating further purification procedures. Moreover, the tertiary amine is disclosed to only act as a promoter for those aromatic aldehydes containing free hydroxy groups. The present invention overcomes these problems by using as a promoting agent a tertiary amine-containing resin.

The tertiary amine-containing resin has the general formula:

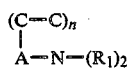

wherein A and $R_1$ are each independently alkyl, alkenyl, alkynyl, substituted alkyl, substituted alkenyl, or substituted alkynyl, aryl, substituted aryl, alkaryl, or aralkyl, and n is a number from about 100 to about 1,000,000.

Examples of suitable amine containing resins include tertiary amine-containing polystyrenes with and without divinylbenzene crosslinking, tertiary amine-containing polyacrylates, tertiary amine-containing polyethylenes, tertiary amine-containing styrene-maleic anhydride copolymers, tertiary amine-containing ethylene-maleic anhydride copolymers, and tertiary amine-containing polypropylenes. Particularly suitable tertiary aminecontaining resins are the dimethylated-aminomethylated polystyrene resins sold under the name AMBERLYST ® by Rohm and Haas or those sold under the name DOWEX ® by Dow Chemical.

The most preferred resins are the divinylbenzene crosslinked types with macroreticular or macroporous type of structure. Examples of these resins include the IRA-35 Rohm and Haas AMBERLYST ® resin and the MWA-1 Dow Chemical DOWEX ® resin.

The amount of tertiary amine-containing resin used as a promoting agent can range from about 10 to about 200 wt. % based upon the amount of aromatic aldehyde-containing polymer used.

Utilization of a less expensive tertiary amine-containing resin as a promoting agent alto allows the use of less of the more expensive aldehyde-containing resin. Thus, a surprising and unexpected advantage is achieved since the overall cost of an efficient racemization process is greatly reduced.

Another surprising advantage of using a tertiary amine-containing resin as a promoting agent resides in the fact that the resin functions as an effective promoting agent in the presence of aromatic aldehyde-containing polymers which do not contain free hydroxyl groups or ether groups. Thus, the tertiary amine-containing resins can be used as promoting agents for a wide variety of aldehyde-containing racemization agents including but not limited to resins made from the reaction between salicylaldehydes and chloromethylated polyvinylbenzenes in the presence of a base.

When the promoting agent is present, the racemization reaction of the present invention is carried out under the previously described reaction conditions in regard to temperature, pressure, and other parameters. Use of the promoting agent allows a greater degree of racemization to be accomplished in shorter time periods, at least 1 to 2 hours faster than racemization reactions carried out in the absence of a promoting agent.

The racemized amino acid obtained through any of the processes of the present invention can then be subjected to further resolution processes to increase the overall yield of the desired amino acid. Resolved amino acids have many well known uses. For instance, L-phenylalanine is a precursor for the artificial sweetener aspartame. The racemization processes of the present invention can also be utilized in connection with processes for resolving racemic mixtures such as D,L-phenylalanine.

The present invention will be further illustrated in the Examples which follow.

COMPARATIVE EXAMPLE 1

This comparative example shows the loss of activity of a pyridoxal phosphate upon prolonged storage. A 4 percent by weight solution of methyl-D-phenylalaninate ester in toluene was stirred and refluxed with a 15 percent by weight, based upon the D-ester content, of a six month old preparation of pyridoxal phosphate on a N,N-diethylaminoethyl modified cellulose ion exchange resin (DEAE Bio-Gel A from Bio-Rad Labs). After 19 hours at reflux, there was no change in optical rotation as measured by a polarimeter.

COMPARATIVE EXAMPLE 2

The cellulose supported pyridoxal phosphate of Comparative Example 1 was reprepared and used fresh at the 50 percent by weight level based on the D-phenylalanine ester content. After 32.5 hours of refluxing and stirring, only 17 percent racemization had occurred.

COMPARATIVE EXAMPLES 3–5

Comparative Example 2 was repeated with 100 and with 10 mole percent acetic acid (based on D-ester content) also present. Complete racemization was observed in 7 hours in both cases but there was considerable peptidization of the phenylalanine ester to a gummy, insoluble di- and/or polypeptide. When 100 mole percent of acetic acid was used, the peptide started to precipitate in less than 1 hour. When this was done in the presence of 100 mole percent, based on D-phenylalanine ester content, of hydrochloric acid, that is using the D-phenylalaninate hydrochloride, no peptidization was observed. However, an extra step was necessary to neutralize the racemized, or D,L-phenylalanine ester hydrochloride before the D,L-phenylalaninate ester could be used in an enzymatic resolution process.

EXAMPLE 1

A. Preparation of Resin

The procedure used is based upon H. W. Gibson and F. C. Bailey, J. Polymer, Sci., Polymer. Chem. Ed. 12 2141 (1974). A charge of 538 grams of chloromethylated BIOBEADS® S-X1 (10 percent divinylbenzene, 4.25 $CH_2Cl$ meq/g, (2.65 mole) Bio-Rad Labs) was added to the potassium phenolate salt of salicylaldehyde formed from 185.5 grams of 85 percent KOH and 404 grams salicylaldehyde (1:1 mole ratio KOH/salicylaldehyde) in 3 liters of KOH-dried and distilled dioxane and 4 liters of 2B ethanol. The amount of the potassium salt of salicylaldehyde used was 20 percent in excess over the amount of chloromethyl groups. The suspension was stirred and refluxed for 18 hours. The resin was then filtered and washed, first with distilled water, then with 2B ethanol, then with dioxane and finally with tetrahydrofuran. The resin was then vacuum oven dried at 60° C. The yield was 98 percent. The resin showed strong absorption in the infrared at 1684 $cm^{-1}$, and at 2756 and 2852 $cm^{-1}$ corresponding to the aldehyde groups. Ether absorption bands were also present. There was only weak absorption for $CH_2Cl$ at 699 $cm^{-1}$.

B. Racemization

A toluene solution of the methyl D-phenylalaninate ester derived from an enzymatic resolution process is treated with the above resin at reflux temperature with stirring until there is no longer any significant optical activity. The extent of the racemization reaction is followed by the use of a polarimeter. On a small scale (100 milliliter vessel), the racemization with 25 milliliters of a 5.8 weight percent solution of methyl-D-phenylalaninate in toluene and 0.58 grams of resin is complete in 8 to 10 hours. The resin is then filtered from the solution and recycled for a new batch. In this manner, it was demonstrated that there was no loss of activity after 5 recycles. There was no evidence of any peptidization occurring.

EXAMPLE 2

A. Preparation of Resin

The preparation of the resin was similar to that in Example 1 except 6.1 grams of poly(vinylbenzyl chloride) (Polyscience, Inc. No. 7055), (0.040 mole $CH_2Cl$), 6.9 grams of 2,4-dihydroxybenzaldehyde (0.050 mole) and 3.2 grams of 87 percent KOH (0.050 mole) were used. The worked-up resin sshowed CHO, ether and $CH_2Cl$ absorption peaks in the infrared region.

B. Racemization

The racemization was carried out essentially as described in Example 1. The results were essentially those seen in Example 1.

COMPARATIVE EXAMPLE 6

This comparative example shows the necessity of the hydroxy group on the aromatic ring for making the racemization catalyst.

A. Preparation of Resin

Poly(vinylbenzyl chloride) resin was oxidized to poly(vinylbenzaldehyde) $\{CH_2-CH-(C_6H_4-CHO)\}_n$ with dimethyl sulfoxide and sodium bicarbonate according to the procedure of H. W.Gibson, and F. C. Bailey, J. Polymer. Sci., Polymer. Chem. Ed. 13, 1951–55 (1975).

B. Racemization

The above prepared resin gave slow racemization with the same procedure as in Example 1, 64 percent in 9.5 hours, 73 percent in 14.5 hours, 83 percent in 24 hours and 86 percent in 30.5 hours. When the resin was used with a small amount of glacial acetic acid, the racemization was complete in 7 hours but a considerable amount of precipitation due to peptidization was observed. The use of less resin, 0.1 gram versus 0.5 gram, showed even slower racemization.

EXAMPLE 3

A. Preparation of Resin

The procedure was essentially that of Example 2 except 8.35 grams of 5-nitrosalicylaldehyde was used in place of 6.9 grams of dihydroxybenzaldehyde. The prepared resin showed strong CHO, ether, and $NO_2$ absorptions and weak $CH_2Cl$ absorption in the infrared region.

B. Racemization

The procedure was that of Example 1. In 12.5 hours, 80 percent racemization was observed. Complete racemization was seen in 19.5 hours.

COMPARATIVE EXAMPLE 7

A. Preparation of Resin

The resin was prepared by following the procedure of K. Toi et al., Bull. Chem. Soc. Jpn. 36, 734–38 (1963). Poly(para-aminostyrene) was converted to the diazonium salt with nitrous acid and then the diazonium salt was coupled with salicylaldehyde. The thus-produced resin had the structure $-[CH_2-CH(C_6H_4N=NC_6H_3(OH)CHO)]-_n$. Infrared analysis showed strong CHO and OH absorption bonds.

B. Racemization

The racemization procedure was that of Example 1. The result was an irreversible reaction of the resin with the L-phenylalaninate amino group. Some peptidization was also observed.

EXAMPLE 4

This Example shows the effect of using a tertiary amine-containing resin as a promoting agent. 0.58 grams of the resin of Comparative Example 6 was used for the racemization of 25 milliliters of a 5.8 weight percent toluene solution of methyl-D-phenylalaninate. To the racemization mixture was also added 0.58 gram of Rohm and Haas macroreticular AMBERLYST® IRA-35 ion exchange resin $[CH_2-CH(C_6H_4CH_2N(CH_3)_2)]_n$. Complete racemization occurred in 19.5 hours. Without the tertiary amine-containing resin present, only 86 percent racemization was observed in 30.5 hours.

EXAMPLE 5

The procedure was essentially that of Example 1. In addition to the above prepared racemization catalyst, there was added 0.58 gram of the AMBERLYST® IRA-35 resin. Complete racemization was observed in 6 hours versus 8–10 hours without the tertiary amine-containing resin present.

COMPARATIVE EXAMPLE 8

Using only the AMBERLYST® IRA-35 resin or a similar resin, DOWEX® MWA-1, no racemization was observed.

Additional features of the preferred and most preferred embodiments of the present invention are found in the claims hereinafter.

What is claimed is:

1. A racemization catalyst for amino acids having the structure:

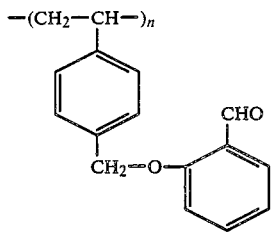

wherein n is an integer from 100 to about 1,000,000.

2. A process for the production of the racemization catalyst of the structure

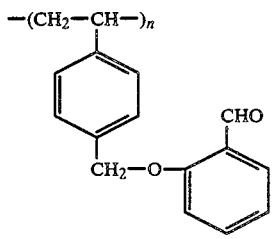

wherein n is an integer from 100 to about 1,000,000, which comprises reacting a hydroxy aromatic aldehyde with a choroalkylsubstituted vinylbenzene polymer in the presence of a base.

3. The process according to claim 2 wherein the hydroxy aromatic aldehyde is salicylaldehyde.

4. The process according to claim 2 wherein the chloroalkylsubstituted vinylbenzene polymer is poly(vinylbenzyl chloride).

5. The process according to claim 2 wherein the chloroalkyl-substituted vinylbenzene polymer is poly(vinylbenzyl chloride) crosslinked with divinylbenzene.

6. The process according to claim 2 wherein the base is selected from the group consisting of potassium hydroxide, sodium hydroxide, pyridine, triethylamine and lithium hydroxide.

* * * * *